United States Patent [19]

Portlock

[11] 4,075,132
[45] Feb. 21, 1978

[54] METHOD OF PREPARING β-DIHYDROTHEBAINE

[75] Inventor: David Edward Portlock, Woburn, Mass.

[73] Assignee: Sharp Associates, Cambridge, Mass.

[21] Appl. No.: 757,460

[22] Filed: Dec. 23, 1976

Related U.S. Application Data

[62] Division of Ser. No. 624,666, Oct. 22, 1975, Pat. No. 4,025,521.

[51] Int. Cl.$^2$ .......................................... C07D 221/28
[52] U.S. Cl. .................................................... 260/285
[58] Field of Search ......................................... 260/285

[56] References Cited

U.S. PATENT DOCUMENTS

| | | | |
|---|---|---|---|
| 3,085,091 | 4/1963 | Sawa et al. | 260/285 |
| 3,474,101 | 10/1969 | Bentley | 260/285 |

OTHER PUBLICATIONS

Bentley et al. (I), J. Chem. Soc., pp. 958–966 (1952).
Bentley et al. (II), J. Chem. Soc. (C), pp. 1945 & 1946 (1969).
Schmid et al., Helv. Chim. Acta., vol. 33, pp. 863–873 (1950).

*Primary Examiner*—Donald G. Daus
*Assistant Examiner*—D. B. Springer
*Attorney, Agent, or Firm*—Louis E. Davidson

[57] ABSTRACT

The reaction of thebaine or dihydrothebaine-φ with potassium in liquid ammonia respectively in the absence or presence of catalyst yields β-dihydrothebaine.

2 Claims, No Drawings

METHOD OF PREPARING β-DIHYDROTHEBAINE

This is a division of application Ser. No. 624,666, filed Oct. 22, 1975, now U.S. Pat. No. 4,025,521 issued May 24, 1977.

BACKGROUND OF THE INVENTION

1. Field of the Invention

β-dihydrothebaine has the structural formula,

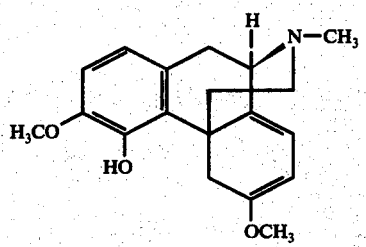

is a member of the morphine alkaloid family in general, and is a derivative of thebaine in particular. Thebaine, a natural alkaloid, has the following structure:

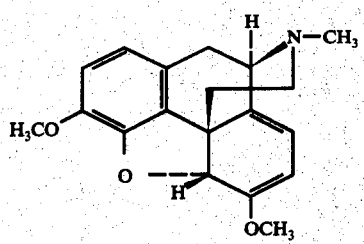

In formulas I and II, as elsewhere in this specification, a dashed line represents a covalent bond projecting below the plane of a reference atom while a wedged or heavily-accented line signifies a covalent bond projecting above such plane. Both β-dihydrothebaine and thebaine are important intermediates in the synthesis of analgesic narcotic antagonist compounds. For a thorough review of the field, refer to: Bentley, K. W., *The Chemistry of the Morphine Alkaloids,* Chapters XII and XV, London, Oxford, 1954; and Bentley, K. W., "The Morphine Alkaloids", in: *The Alkaloids,* Vol. XIII, Manske, R.H.F. (Ed.), Chapter 1, New York, Academic Press, 1971.

2. The Prior Art

Schmid and Karrer (Helv. Chim. Acta, 33:873 [1950]; hereafter "*Schmid*") report that reduction of thebaine with LiAlH₄ in benzene and ether results in a 42% yield of β-dihydrothebaine.

Bentley, Lewis and Taylor (J. Chem. Soc., C, 1945 [1969]; hereafter "*Bentley I*"), however, find the Schmid reaction unsatisfactory: large amounts of thebaine remain unreacted even after the reaction proceeds for more than 48 hours; the process yields phenolic products othr than β-dihydrothebaine; and the yield report in *Schmid* is not reproducible. *Bentley I* further describes the results of studies in the reduction of thebaine utilizing mixtures of LiAlH₄ and AlCl₃. Lithium aluminum hydride and aluminum chloride at respective ratios of 1:1, 1:3, or 1:4 provide neodihydrothebaine,

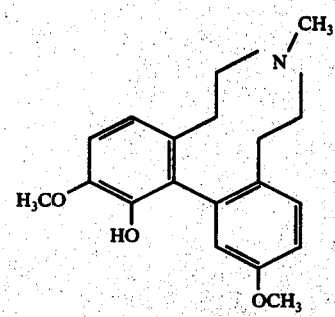

as the major product; and traces of thebaine-A enol methyl ether,

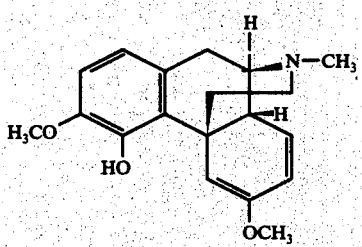

On the other hand, LiAlH₄ and AlCl₃ at respective ratios of 4:1 to 3:1 yield thebaine-A enol methyl ether, IV, as the principle product and traces of neohydrothebaine (III), β-dihydrothebaine (II), and an unidentified C-4 phenolic compound.

Bentley, Robinson, and Wain (J. Chem. Soc., 958 [1952]; hereafter "*Bentley II*") elucidate the structure of dihydrothebaine-φ,

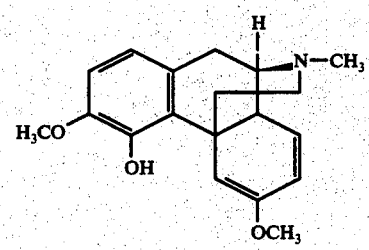

and communicate that reaction of thebaine with sodium in liquid ammonia results in a 95% yield of dihydrothebaine-φ without trace of the β-dihydrothebaine isomer.

Birch and Friton (Aust. J. Chem., 22:971 at 972 [1966]; hereafter "*Birch*") disclose that: "Reduction of thebaine with sodium in liquid ammonia opens the ether ring, but the resulting methoxycyclohexadine [i.e., dihydrothebaine-φ] has unconjugated double bonds *which cannot be readily conjugated by the usual basic reagents.* (emphasis supplied)." The *Birch* reference thus teaches that isomerization of dihydrothebaine-φ (V) to β-dhydrothebaine (I) will not proceed with alkali metal amides in liquid ammonia.

Table A provides a synopsis of the preceding prior art. This analysis of the prior art thus indicates that there is no current simple, satisfactory method for producing β-dihydrothebaine is reasonably good yields.

Table A

| | Summary of Reactions Disclosed by Prior Art | | |
|---|---|---|---|
| Reference | Starting Material | Reactants | Product |
| Schmid | | LiAlH$_4$ LiAlH$_4$ — AlCl$_3$ (1:1, 1:3, or 1:4) | β-dihydrothebaine (42%)* neodihydrothebaine (III) and trace of thebainone-A enol methyl ether (IV) |
| Bentley I | Thebaine (II) | LiAlH$_4$ — AlCl$_3$ (4:1 or 3:1) | neohydrothebaine (III) and traces of β-dihydrothebaine (I) |
| Bentley II | | Na — liq NH$_3$ | dihydrothebaine-φ (V) |
| Birch | dihydrothebaine-φ (V) | Na — liq NH$_3$ | None |

*Disputed by Bentley I

SUMMARY OF THE INVENTION

The subject matter of this reaction is a method of preparing β-dihydrothebaine by reacting thebaine (II) with potassium in liquid ammonia in the absence of catalysts or by reacting dihydrothebaine-φ (V) with potassium in the presence of catalyst. When thebaine is the starting material, the method effects 95% conversion thereof and yields a 1:1 reaction mixture of β-dihydrothebaine and dihydrothebaine-φ. When dihydrothebaine-φ is the starting compound, the method converts 50% of that compound to β-dihydrothebaine; no side reactions occur.

The method is straghtforward. Thebaine (II) is added to a solution of potassium in an excess of liquid ammonia; 1 to 3 equivalents of potassium are utilized to 1 equivalent of starting material, although 2.3 equivalents of the former are preferred. The reaction is allowed to proceed for a period of about 0.5 to 3 hours, which period represents a convenient rather than a critical time. The reaction, of course, proceeds at liquid ammonia temperature ranges of approximately $-78°$ C to approximately $-33°$ C. At the end of the reaction, unused potassium, if any, is removed by addition of a small quantity of any suitable organic reagent, such as ethanol or diethyl ether. Beta-dihydrothebaine is easily isolated from the neutralized reaction mixture by a suitable organic solvent for that compound. Such solvents are well-known in the art as disclosed in the cited references. Use of potassium without catalysis (e.g. by ferric cation) in the method is a key factor.

Comparative studies of the reaction of thebaine with related elements, e.g., lithium, sodium, or calcium or with potassium catalyzed by ferric chloride show that the reaction yields dihydrothebaine-φ rather than β-dihydrothebaine. Example 3, below, provides details of comparative experiments involving the process; Table B summarizes the results of those experiments.

Table B

| | Reaction of Thebaine with Alkali Elements in Liquid Ammonia | | | | |
|---|---|---|---|---|---|
| Example No. | Element | Equivalents | Thebaine Converted-% | % I | % V |
| 1 | K | 1.0 | 50* | 50 | 50 |
| 1 | K | 2.3 | 95 | 50 | 50 |
| 3A | Ca | 2.3 | 50* | 0 | 100 |
| 3B | Li | 2.3 | 62 | 0 | 100 |
| 3C | K/FeCl$_3$ | 2.3 | 95 | 0 | 100 |
| — | Na** | 2.3 | 95 | 0 | 100 |

*50% of unreacted thebaine recovered
**results reported in Bentley II

Alternately, dihydrothebaine-φ (V) is added to a solution of potassium in an excess of liquid ammonia in the presence of a catalyst such as Fe(NO$_3$)$_3$.9H$_2$O, FeCl$_3$, or similar catalysts known to the art: see. for example, Fieser L. F. and Fieser, M., *Reagents for Organic Synthesis, Vol. I*, New York, J. Wiley & Sons, 1967. Three to five equivalents of potassium to 1 equivalent of dihydrothebaine-φ are utilized, although 3 equivalents of the former are preferred. Reaction parameters, such as temperature and time of reaction, and solvents for isolation of the product of the reaction, β-dihydrothebaine, are identical to those described above. Details of the reaction are provided in Example 2, below.

The disclosed method, therefore, affords a convenient reliable means for virtually quantitative conversion of thebaine or dihydrothebaine-φ to β-dihydrothebaine in surprisingly high yields.

DESCRIPTION OF THE PREFERRED EMBODIMENT

EXAMPLE 1

Reaction of Thebaine with Elemental Potassium in Liquid Ammonia in the Absence of Catalyst The apparatus utilized in the following procedure was a one-liter, three-necked flask fitted with: a mechanical stirrer; a reflux condenser which in turn was adapted with a drying tube (KOH); a ground glass stopper; and a heating mantle for insulation. Approximately 600 ml of liquid ammonia were introduced to the flask; 44.0 g (0.141 mol) of thebaine were then added to the ammonia, resulting in a sand colored mixture. While the mixture being stirred, 12.6 g (0.322 mol; 2.3 equivalents) of elemental potassium were added slowly (0.5 to 3 hours). As the potassium was being added, the resulting mixture first became orange in color, which eventually turned dark red. The reaction mixture then was stirred for 1 hour, the latter time being not critical but convenient. The reaction was then quenched by addition of 24 ml of absolute ethanol resulting in a dark brown solution. The solution was stirred for an additional 0.5 hour, and the ammonia was allowed to evaporate overnight. Neither the reaction time nor the method of eliminating the liquid ammonia are critical to the process; the ammonia, for example, might have been driven off by controlled heating. After evaporation of the ammonia, 500 g of crushed ice and 150 ml of water were slowly added to the reaction mixture which then assumed a green color. The mixture was then treated with solid carbon dioxide which precipitated the reaction products from the mixture. Two liters of ether then were added to the mixture; a very small interface was filtered by gravity, and the layers separated. The ether layer was washed four times with 250 ml of water, dried (Na$_2$SO$_4$), and concentrated to yield a tan foam. The latter was dried under high vacuum, and 35.7 g of a tan powder was obtained. Analysis of that product by nuclear magnetic resonance (NMR) revealed it to be a 1:1 mixture of β-dihydrothebaine (olefinic protons: d, 1H, 5.73 ppm; and d, 1H, 4.80 ppm) and dihydrothebaine-φ (olefinic protons: s, 1H, 6.10 ppm; and t, 1H, 5.57 ppm). That mixture was boiled in 250 ml of ligroin (b.p., 63°–75° C), and then ethyl acetate was added until the solution was complete. The solution was filtered while still hot and the filtrate was allowed to come to room temperature. Fifteen gm (24% overall yield) of β-dihydrothebaine (free of dihydrothebaine-φ by NMR analysis) were thus obtained.

Utilization of 5.48 g (1 equivalent) of potassium in the above process provided a 1:1 mixture of β-dihydrothebaine and dihydrothebaine-φ, but only 50% of the thebaine was reduced.

EXAMPLE 2

Reaction of Dihydrothebaine-φ with Potassium in Liquid Ammonia in the Presence of Catalyst Apparatus utilized in this example was similar to that described in preceding Example 1 except that a 100 ml flask was used. Approximately 65 ml of liquid ammonia and a catalytic amount of $Fe(NO_3)_3 \cdot 9H_2O$ were added to the flask followed by the slow addition of 750 mg (19.2 mmol; 3 equivalents) of potassium: the resulting solution, which was steel-grey in color, was then stirred for approximately 0.5 hour; the latter period of time was not critical but rather convenient. Addition of 2.0 g (6.4 mmol) of dihydrothebaine-φ turned the reaction mixture to a red color which was indicative of presence of the di-anion. The reaction mixture was then stirred for approximately 2 hours, a convenient rather than critical period of time. Addition of 10 ml of diethyl ether quenched the reaction. Ten ml of 20% aqueous diethyl ether solution was then added. The ammonia was evaporated under a fume hood. An additional quantity of aqueous diethylether and an excess of solid ammonium chloride were added to the reaction mixture. Aqueous and ethereal layers were separated. The aqueous phase was extracted once with diethyl ether. Ethereal phases were combined, washed twice with water, and dried over anhydrous sodium sulfate. Concentration under reduced pressure left 1.58 g (79% yield) of a red resin, the NMR spectrum of which indicated a 1:1 mixture of β-dihydrothebaine and dihydrothebaine-φ.

EXAMPLE 3

Comparative Reactions of Thebaine in Liquid Ammonia Respectively with: (a) Calcium; (b) Lithium; and (c) Potassium Catalysed by the Presence of Ferric Cation In the succeeding examples, the apparatus utilized was that described in Example 1.

A. Reaction of Thebaine with Calcium in Liquid Ammonia.

Approximately 250 ml of liquid ammonia was added to the raction flask containing 22.0 g (0.01 mol) of thebaine. To that mixture 3.2 g (0.081 mol; 2.3 equivalent) of elemental calcium were added slowly. The reaction mixture turned a red color, and was stirred for 1⅔ hours. Eight ml of absolute ethanol were then added, and the reaction mixture was then poured into a 1-liter beaker containing 500 g of crushed ice. The reaction mixture was then acidified by addition of solid carbon dioxide and subsequently extracted with 1800 ml of ether and 400 ml of chloroform. The combined organic solvent layer was washed with water and dried over anhydrous sodium sulfate. Filtration and concentration yielded 19.2 g of a reddish solid. NMR analysis revealed a 1:1 mixture of unreacted thebaine and dihydrothebaine-φ. The solid was extracted with ether and only the dihydrothebaine-φ dissolved. In this manner a 50% yield of dihydrothebaine-φ and a 50% recovery of unreacted thebaine was obtained. No β-dihydrothebaine was produced.

B. Reaction of Thebaine with Lithium in Liquid Ammonia

Forty-four g (0.141 mol) of thebaine and 500 ml of anhydrous liquid ammonia were independently added to the reaction flask, giving a tan-colored mixture. After slow addition of 2.2 g (0.32 mol; 2.3 equivalent) of metallic lithium, the reaction mixture was stirred for 1.5 hours, and thereafter the reaction was quenched with 5 ml of absolute ethanol. After evaporation of the ammonia, the remaining residue was dissolved in 500 ml of water and acidified with solid carbon dioxide. A solid precipitated which was dissolved in ether. The ether extract was washed with water, dried (anhydrous sodium sulfate), filtered, and concentrated, yielding 27.2 g (0.087 mol; 62% yield) of dihydrothebaine-φ, the identity of which was confirmed by NMR. No β-dihydrothebaine was produced.

C. Reaction of Thebaine with Potassium in Liquid Ammonia Catalyzed by Ferric Chloride Twenty-two g of thebaine (0.07 mol) was added to the reaction flask which was cooled to −78° C; 250 ml of liquid ammonia and some crystals of ferric chloride were then added to the flask, followed by 6.3 g (0.161 mol; 2.3 equivalent) of potassium. That reaction mixture was stirred for 1 hour and assumed an orange color. Addition of 8 ml of absolute ethanol quenched the reaction. After evaporation of the ammonia, 500 ml of water was added to the reaction mixture followed by solid carbon dioxide. Subsequent extraction with ether, washing with water, drying, filtration and concentration gave a 90% yield of dihydrothebaine-φ, verified as such by NMR analysis. No β-dihydrothebaine was produced.

What is claimed is:

1. A method of producing β-dihydrothebaine, which method comprises:
    the step of isomerizing dihydrothebaine-φ to β-dihydrothebaine with 3–5 equivalents of potassium in liquid ammonia with a ferric-ion catalyst.
2. The method as in claim 1 wherein the catalyst is $Fe(NO_3)_3 \cdot 9H_2O$.

* * * * *